United States Patent [19]

Junino et al.

[11] Patent Number: 5,034,015
[45] Date of Patent: Jul. 23, 1991

[54] PROCESS FOR DYEING KERATIN FIBRES WITH A MONOHYDROXYINDOLE ASSOCIATED WITH AN IODIDE AND HYDROGEN PEROXIDE

[75] Inventors: Alex Junino, Livry-Gargan; Gerard Lang, Saint-Gratien; Jean J. Vandenbossche, Aulnay-sous-Bois, all of France

[73] Assignee: L'Oreal, Paris, France

[21] Appl. No.: 404,512

[22] Filed: Sep. 8, 1989

[30] Foreign Application Priority Data

Sep. 12, 1988 [LU] Luxembourg .................... 87336

[51] Int. Cl.$^5$ .................... A61K 7/13; A61K 31/40; C09B 7/02; D06P 3/08
[52] U.S. Cl. .................... 8/423; 8/405; 8/429; 8/431; 548/484
[58] Field of Search .................... 8/423, 429

[56] References Cited

U.S. PATENT DOCUMENTS

| | | | |
|---|---|---|---|
| 4,013,404 | 3/1977 | Parent et al. | 8/423 |
| 4,776,857 | 10/1988 | Carroll et al. | 8/423 |
| 4,804,385 | 2/1989 | Grollier et al. | 8/423 |
| 4,808,190 | 2/1989 | Grollier et al. | 8/423 |
| 4,822,375 | 4/1989 | Lang et al. | 8/423 |
| 4,885,006 | 12/1989 | Grollier et al. | 8/423 |
| 4,888,027 | 12/1989 | Grollier et al. | 8/423 |

FOREIGN PATENT DOCUMENTS

| | | |
|---|---|---|
| 0271186 | 6/1988 | European Pat. Off. |
| 2197885A | 11/1986 | United Kingdom |
| 2185498A | 7/1987 | United Kingdom |
| 2186891A | 8/1987 | United Kingdom |

OTHER PUBLICATIONS

Biochem. Methods, vol. 89, 1978, p. 249, No. 89:38872m, Mori et al, Gas Chromatography of 5-Hydroxy-3-Methylindole in Human Urine.
Chemical Abstracts, vol. 74, 1971, p. 444, No. 131857k, Marchelli et al, Mass Spectra of the Hydroxyindole-3-Carboxylic Acids and the Hydroxyskatoles.
Pharmacodynamics, vol. 69, 1968, p. 3215, No. 3450j, Mattok et al, The Metabolism of Hydroxyskatoles in Rats.

*Primary Examiner*—A. Lionel Clingman
*Attorney, Agent, or Firm*—Cushman, Darby & Cushman

[57] ABSTRACT

Process for dyeing keratin fibres consisting in applying on these fibres a composition (A) containing at least one indole colorant of formula:

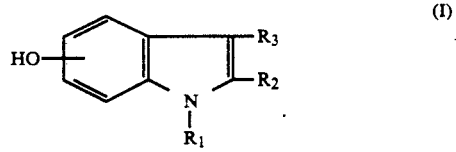

(I)

where
$R_1 = H$ or $C_1-C_4$ alkyl;
$R_2$ and $R_3$, which may be identical or different, denote H, $C_1-C_4$ alkyl, carboxyl or alkoxycarbonyl; or a salt or a precursor of a compound (I), associated, either with iodide ions, or with $H_2O_2$; application of composition (A) being preceded or followed by the application of a compound (B) which contains, either $H_2O_2$ at a pH of 2 to 12 when (A) contains iodide ions, or iodide ions at a pH of 2 to 11 when (A) contains $H_2O_2$.

This process allows particularly powerful and resistant dyes to be made.

30 Claims, No Drawings

PROCESS FOR DYEING KERATIN FIBRES WITH A MONOHYDROXYINDOLE ASSOCIATED WITH AN IODIDE AND HYDROGEN PEROXIDE

The invention relates to a new process for colouring keratin fibers, and more particularly human keratin fibers, such as hair, with a monohydroxyindole associated with iodide ions, and to the compositions used in this process.

The dyeing of hair with hydroxylated indole derivatives has already been proposed in the past, in particular in U.S. Pat. No. 4,013,404, as well as in Patent FR-A-2,252,841, and in German Patent Application DE-A-3,031,709.

In these prior processes, when the dyes are used as oxidation dyes, oxidation agents such as hydrogen peroxide or different persalts are generally used to develop a color.

These state of the art processes, however, have a certain number of disadvantages in that they lead to weak hues in spite of long exposure times, or to surface dyes which have very little resistance to external agents such as bad weather or sun, or even to shampoos and to perspiration.

The applicants has just discovered, which is the subject of the present invention, that by associating iodide ions with a monohydroxyindole defined below, it is possible to obtain, in a surprising manner, particularly powerful and resistant dyes. The association allows, in addition, good coverage of white hair, better compatibility and a less selective dye to be obtained.

The subject of the invention is therefore a dyeing process using a monohydroxyindole and iodide ions in the presence of hydrogen peroxide.

Another subject of the invention is constituted by compositions used in this process, as well as dyeing kits or sets with several compartments, containing the different components intended to be used in the process according to the invention.

Other subjects of the invention will appear on reading the description and the examples which follow.

The process of dyeing keratin fibers, preferably human keratin fibers according to the invention, is essentially characterized in that there is applied on these fibers at least one composition (A) containing, in a medium which is appropriate for dyeing, at least one compound of formula (I):

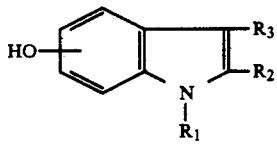

in which:
$R_1$ denotes a hydrogen atom or a $C_1$–$C_4$ alkyl radical;
$R_2$ and $R_3$, which may be identical or different, denote a hydrogen atom, a $C_1$–$C_4$ lower alkyl radical, a carboxyl radical or a $C_1$–$C_4$ alkoxycarbonyl radical;
the OH radical occupies only one of positions 4, 5, 6 or 7 of the aromatic ring,
or at least one of its salts or its precursors, on the condition that when OH occupies position 5, at least one of the radicals $R_1$, $R_2$ or $R_3$ is different from a hydrogen atom, associated either with iodide ions, or with hydrogen peroxide;
application of this composition (A) being preceded or followed by application of a composition (B) which contains, in a medium which is appropriate for dyeing: either hydrogen peroxide at a pH of between 2 and 12, when composition (A) contains iodide ions; or iodide ions at a pH of between 2 and 11, when composition (A) contains hydrogen peroxide.

The hydroxylated derivative (I) can be in its protected form OZ (Z being a $C_2$–$C_6$ acyl group, and preferably Z is an acetyl group), but in this case the pH of composition (A) must be such that the hydroxyl function is liberated.

Among the compounds of the formula (I), the compounds which are particularly preferred are compounds in which the alkyl radical denotes methyl or ethyl; the alkoxycarbonyl radical denotes methyoxycarbonyl or ethoxycarbonyl.

Among the compounds of formula (I) there may be mentioned 6-hydroxyindole, 6-hydroxy-1-methylindole, 6-hydroxymethoxy-3-carbonylindole, 6-hydroxy-1-methyl-3-methoxycarbonylindole, 6-acetoxy-1-methyl-3-methoxycarbonylindole, 6-acetoxy-1-methyl-2,3-dimethoxycarbonylindole, 6-acetoxy-1,2-dimethylindole, 6-hydroxy-1,2-dimethylindole, 6-hydroxy-2-methylindole, 6-hydroxy-2-carboxyindole, 6-hydroxy-2,3-dimethylindole, 6-hydroxy-3-carboxyindole, 6-hydroxy-3-ethoxycarbonylindole, 6-hydroxy-2-ethoxycarbonylindole, 6-acetoxyindole, 6-hydroxy-3-methylindole, 7-hydroxyindole, 4-hydroxyindole, 5-hydroxy-3-methylindole, 7-hydroxy-3-methylindole, 5-hydroxy-2-carboxyindole and 5-hydroxy-2-ethoxycarbonylindole.

Among these, 6-hydroxy-1-methylindole, 5-hydroxy-3-methylindole and 7-hydroxy-3-methylindole are new compounds the syntheses of which will be given below. These new compounds constitute another subject of the invention.

The preferred compounds are 6-hydroxyindole, 4-hydroxyindole, 7-hydroxyindole, 6-hydroxy-1-methylindole, 5-hydroxy-3-methylindole and 5-hydroxy-2-carboxyindole, 7-hydroxy 3-methylindole and 6-hydroxy 2,3-dimethylindole.

The iodide ion used in accordance with the invention is preferably an alkali metal, alkaline-earth metal or ammonium iodide, and more particularly potassium iodide.

The process according to the invention is implemented in a preferential manner by applying, in the first stage, composition (A) containing the iodide ions in the form of an iodide of an alkali metal, an alkaline earth metal or ammonium, and the indole derivatives corresponding to formula (I) defined above, then, in a second stage, after optional intermediate rinsing, composition (B) containing the hydrogen peroxide.

The process according to the invention is preferably applied to the dyeing of hair, and in particular that of living human hair, in which case the medium used must be cosmetically acceptable.

According to a preferred form of implementation the keratin fibers are rinsed between the two stages, which allows, among other things, staining of the scalp to be avoided when the composition is used for dyeing human hair.

The invention can also be carried out without intermediate rinsing, which allows, in particular, the exposure time to be reduced.

Composition (A), which is used in this variant of the process according to the invention, and which constitutes another subject of the latter, is essentially characterized in that it contains at least one indole derivative corresponding to formula (I) defined above and at least some iodide ions in a medium which is appropriate for dyeing.

In the compositions which are used according to the invention, indoles of formula (I) are generally present in proportions of between 0.01 and 5% by weight, preferably between 0.03 and 3% by weight with respect to the total weight of composition (A).

The proportion of iodide ions is preferably between 0.007 and 4% by weight expressed as $I^-$ ions and more particularly between 0.08 and 1.5% by weight expressed as $I^-$ ions, with respect to the total weight of composition (A) or (B).

The hydrogen peroxide content in the hydrogen peroxide solutions used is generally between 1 and 40 volumes, and preferably between 2 and 20 volumes, and more particularly between 3 and 10 volumes.

According to a variant of the process, the pH of the hydrogen peroxide solution is preferably between 2 and 9.

The weight ratio of the indole derivatives of formula (I) to the iodide ions is preferably between 0.05 and 10, and more particularly between 0.5 and 2.

The dyeing process according to the invention is carried out by forecasting exposure times for the different compositions applied in each of the stages of the process, comprised between 10 seconds and 45 minutes, and preferably of the order of 2 to 25 minutes, and more particularly of the order of 2 to 10 minutes.

The applicants have been able to note that dyeing carried out by virtue of the process according to the invention allowed rapid colorations to be obtained which penetrate fibers well, in particular human keratin fibers such as hair, without degrading them. These colors have, in addition, improved resistance to external agents, to shampoos and to perspiration or to permanent-waving treatments.

It has also been possible to notice that hair dyed several times after regrowth was softer, shinier and had better mechanical properties than hair dyed by carrying out the processes of the prior state of the art.

The compositions used in the process according to the invention can be in various forms, such as more or less thickened or gellified liquids, creams, emulsions and foams, and can optionally be packed in aerosol devices or even in other forms which are appropriate for carrying out dyeing.

The appropriate medium for dyeing is preferentially an aqueous medium constituted by water or a water-solvent(s) mixture.

The solvent or the solvents is (are) preferably chosen from the organic solvents which are cosmetically acceptable since they are intended to be used for dyeing human hair. These solvents are chosen in particular from ethyl alcohol, propyl or isopropyl alcohol, tert-butyl alcohol, ethylene glycol, the monomethyl, monoethyl or monobutyl ethers of ethylene glycol or diethylene glycol, ethylene glycol, monomethylether or monoethylether acetate, propylene glycol, the monomethyl ethers of propylene glycol and of dipropylene glycol and methyl lactate.

The particularly preferred solvents are ethyl alcohol, propylene glycol and the monoethyl and monobutyl ethers of ethylene glycol.

According to one form of implementation of the invention, the appropriate medium for dyeing can be constituted by anhydrous solvents, such as those defined above, in this case the composition being either mixed with an aqueous medium at the time of use, or applied to the keratin fibers which have previously been wetted with an aqueous composition.

An anhydrous medium or solvent is called, according to the invention, a medium or a solvent containing less than 1% water.

When the medium appropriate for dyeing is constituted by a water-solvent(s) mixture, the solvents are preferably used at concentrations of between 0.5 and 75% by weight with respect to the total weight of the composition, and in particular between 2 and 50%.

The compositions used according to the invention can also contain any other additives which are normally used for dyeing keratin fibers, and in particular cosmetically acceptable additives, since these compositions are used to dye living human hair.

In these latter cases the compositions can contain, in particular, fatty amides in quantities which are preferably from 0.05 to 10% by weight, anionic, cationic, nonionic or amphoteric surfactants or their mixtures, which are preferably present in proportions of between 0.1 and 50% by weight, thickeners, preferably present in proportions of between 0.1 and 5% by weight, fragrances, sequestering agents, film-forming agents, treatment agents, dispersing agents, conditioning agents, preservatives, opacifying agents and agents which swell keratin fibers.

The thickeners can be chosen from sodium alginate, gum arabic, guar gum, biopolymers, xanthan gum or the scleroglucans, cellulose derivatives, in particular cellulose ethers such as methyl cellulose, hydroxyethyl cellulose and hydroxypropylmethyl cellulose, the sodium salts of carboxymethyl cellulose and optionally cross-linked acrylic acid polymers. Inorganic thickening agents such as bentonite can also be used.

The alkalinizing agents which are capable of being used in these compositions can be, in particular, amines such as alkanolamines or alkylamines, or the alkali or ammonium hydroxides or carbonates.

Acidification agents which are capable of being used in these compositions can be chosen from lactic acid, acetic acid, tartaric acid, phosphoric acid, hydrochloric acid and citric acid.

When the composition is used in the form of a foam it can be packed under pressure in an aerosol device, in the presence of a propulsion agent and of at least one foam generator. The foam generators can be anionic, cationic, nonionic or amphoteric foaming polymers or their mixtures, or surfactants of the type defined above.

These compositions can also contain other colorants which are capable of being used for dyeing keratin fibers and which are known per se, and more particularly 5,6-dihydroxyindole or its derivatives which are described more particularly in FR-A-2,595,245.

It is also possible to introduce into these compositions oxidation colorants chosen in particular from the precursors of oxidation colorants of the para or ortho type, constituted by para-phenylenediamines, para-aminophenols, ortho-aminophenols, ortho-phenylenediamines, heterocyclic bases or even couplers or modifiers chosen in particular from phenols, meta-diphenols, meta-aminophenols, meta-phenylenediamines, mono- or polyhydroxylated derivatives of naphthalene and of aminonaphthalene, pyrazolones and benzomorpholines.

So-called "rapid" oxidation colorants, such as the trihydroxylated derivatives of benzene, the diaminohydroxybenzenes, the aminodihydroxybenzenes or the triaminobenzenes can also be used.

These compositions can also contain direct colorants chosen from the nitrogen-containing derivatives of the benzene series, the anthraquinone colorants, and the naphthoquinone and benzoquinone colorants.

With a view to the implementation of the process according to the invention, the different compositions can be packed in a device with several compartments, also called a dyeing "kit" or set, comprising all the components intended to be applied on the keratin fibers for a single tint, in successive applications with or without premixing.

Such devices are known per se, and can comprise a first compartment containing composition (A) containing the indole derivatives of formula (I) in the presence of iodide ions in a medium which is appropriate for dyeing, and in a second compartment composition (B) based on hydrogen peroxide.

Another form of implementation can consist in providing a first compartment enclosing a composition ($A_1$) containing the monohydroxyindole of formula (I) and a second compartment containing a composition ($A_2$) based on hydrogen peroxide, and a third compartment containing the iodide ions, respectively in the media which are appropriate for dyeing, composition ($A_1$) and composition ($A_2$) being intended to be mixed immediately before application.

A device which is particularly well adapted for the implementation of the invention is constituted by a distributing assembly of the type as those described in FR-A-2,586,913 comprising two separate pouches joined in a flexible case, the two pouches enclosing the compositions as defined above.

The devices with several compartments, which are used according to the invention, can be provided with supplementary compartments, in particular when the media used for composition (A) based on the indole derivative of formula (I) are anhydrous. In this case it is mixed before use with an aqueous support which is appropriate for dyeing and is present in another compartment.

These devices with several compartments, or kits, which are used according to the invention, can be provided with means of mixing at the time of use, which are known per se, and their contents can be packed under an inert atmosphere.

The process and the compositions used according to the invention can be used to dye natural or already dyed hair, whether permanent-waved or not, or straightened, or strongly or slightly bleached hair, optionally permanent-waved. It is also possible to use them for dyeing furs or wool.

The following examples are intended to illustrate the invention without, however, having a limiting character.

PREPARATION EXAMPLE 1

Preparation of 6-hydroxy-1-methylindole

1st stage: Preparation of 6-benzyloxy-1-methylindole

To 125 g of caustic soda in pellets in 125 ml water are added 300 ml toluene, 50 ml methylsulphate and 7.36 g tetrabutylammonium hydrogensulphate, then, with stirring, 0.33 mole (73.6 g) 6-benzyloxyindole. Stirring is maintained for 15 minutes after the end of the evolution of heat. The reaction medium is diluted with two volumes of water. After separation of the organic phase the aqueous phase is extracted with toluene. After washing the organic phases with water and drying them, the desired product is obtained by evaporation. It melts at 79° C.

Analysis of the product obtained after recrystallization from methanol gives the following results:

| Analysis for | Calculated for $C_{16}H_{15}NO$ | Found |
| --- | --- | --- |
| C | 81.01 | 80.92 |
| H | 6.33 | 6.36 |
| N | 5.91 | 5.80 |
| O | 6.75 | 6.99 |

2nd stage: Preparation of 6-hydroxy-1-methylindole

The mixture constituted by 0.24 mole (57 g) 6-benzyloxy-1-methylindole, 5.7 g 10% palladium-on-charcoal, 114 ml cyclohexane and 170 ml 96° ethanol is heated for 30 minutes under reflux. It is filtered hot in order to remove the catalyst. After evaporation of the filtrate under vacuum, an oil is obtained which, when dissolved in isopropyl ether, leads after evaporation to dryness to the desired product. It melts at 74° C.

Analysis of the product obtained gives the following results:

| Analysis for | Calculated for $C_9H_9NO$ | Found |
| --- | --- | --- |
| C | 73.47 | 73.57 |
| H | 6.12 | 6.12 |
| N | 9.52 | 9.39 |
| O | 10.88 | 11.07 |

PREPARATION EXAMPLE 2

Preparation of 5-hydroxy-3-methylindole

1st stage: Preparation of 1-[(5'-benzyloxy-2'-nitro)phenyl]-2-cyanopropane

The reaction mixture constituted by 0.3 mole (80.4 g) 5-benzyloxy-2-nitrophenylacetonitrile, 63.9 g methyl iodide and 186.3 g potassium carbonate in 300 ml acetone is taken to reflux temperature for 6 hours. The reaction mixture is diluted with 2 kg of iced water containing 400 ml concentrated hydrochloric acid. The desired product crystallises. After recrystallization from alcohol, it melts at 79° C.

Analysis of the product obtained gives the following results:

| Analysis for | Calculated for $C_{16}H_{14}N_2O_3$ | Found |
| --- | --- | --- |
| C | 68.08 | 68.23 |
| H | 4.96 | 4.92 |
| N | 9.93 | 9.93 |
| O | 17.02 | 16.88 |

2nd stage: Preparation of 5-hydroxy-3-methylindole 80 g 1-[(5'-benzyloxy-2'-nitro)phenyl]-2-cyanopropane are heated to 75° C. for one hour under 8 bars of hydrogen in the presence of 16 g 10%, palladium-on-charcoal in 1 l ethanol to which have been added 100 ml acetic acid. After cooling the catalyst is filtered off. The filtrate is concentrated and diluted with 500 ml ethyl acetate. The ethyl acetate phase is washed with water. The desired product is obtained by evaporation of the ethyl acetate. After recrystallization from alcohol, it melts at 116° C.

Analysis of the product obtained gives the following results:

| Analysis for | Calculated for C$_9$H$_9$NO | Found |
| --- | --- | --- |
| C | 73.45 | 73.45 |
| H | 6.16 | 6.12 |
| N | 9.52 | 9.48 |
| O | 10.87 | 11.08 |

PREPARATION EXAMPLE 3

Preparation of 7-hydroxy-3-methylindole

1st stage: Preparation of 1-[(3'-benzyloxy-5'-chloro-2'-nitro)phenyl]-2-cyanopropane The reaction mixture constituted by 0.5 mole (151.2 g) 3-benzyloxy-5-chloro-2-nitrophenylacetonitrile, 152.6 g methyl iodide and 207 g potassium carbonate in 500 ml acetone is taken to reflux temperature for 8 hours. The reaction medium is diluted with 4 kg iced water to which have been added 500 ml acetic acid. The desired product precipitates. After recrystallization from acetic acid, it melts at 180° C.

Analysis of the product obtained gives the following results:

| Analysis for | Calculated for C$_{16}$H$_{13}$N$_2$O$_3$Cl | Found |
| --- | --- | --- |
| C | 60.67 | 60.72 |
| H | 4.14 | 4.12 |
| N | 8.84 | 8.64 |
| O | 15.15 | 15.01 |
| Cl | 11.19 | 11.34 |

2nd stage: Preparation of 7-hydroxy-3-methylindole

The reaction mixture constituted by 20 g 1-[(3'-benzyloxy-5'-chloro-2'-nitro)phenyl]-2-cyanopropane and 10 g 10% palladium-on-charcoal in 100 ml ethanol to which have been added 40 ml cyclohexane is heated under reflux for 4 hours. At the end of the reaction the catalyst is separated from the reaction medium by filtration. After addition of carbon black to the filtrate, filtration and then evaporation, the desired product, which crystallizes from an isopropylether-chloroform mixture, is obtained. It melts at 190° C.

Analysis of the product obtained gives the following results:

| Analysis | Calculated for C$_9$H$_9$NO | Found |
| --- | --- | --- |
| C | 73.45 | 73.53 |
| H | 6.16 | 6.23 |
| N | 9.52 | 9.45 |
| O | 10.87 | 10.76 |

APPLICATION EXAMPLES

EXAMPLE 1

| | |
| --- | --- |
| 6-Hydroxyindole | 2.0 g |
| Potassium iodide | 1.0 g |
| Ethyl alcohol | 15.0 g |
| Citric acid qs pH = 1.8 | |
| Water qs | 100.0 g |

This composition is applied on grey hair containing 90% white hair for 5 minutes.

A pH 3 solution of hydrogen peroxide measuring 12.5 volumes is then applied to this hair without intermediate rinsing. The hair is rinsed and dried. The hair is dyed a chestnut hue.

EXAMPLE 2

| | |
| --- | --- |
| 6-Hydroxyindole | 2.0 g |
| Potassium iodide | 1.0 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Caustic soda qs pH = 9 | |
| Water qs | 100.0 g |

This composition is applied on grey hair with 90% white hair for 5 minutes. After rinsing, a pH 3 solution of hydrogen peroxide measuring 12.5 volumes is applied on the hair for 10 minutes. After rinsing and drying, the hair is dyed a pearly blonde hue.

EXAMPLE 3

| | |
| --- | --- |
| 6-Hydroxyindole | 1.0 g |
| Potassium iodide | 1.0 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Spontaneous pH = 6.7 | |
| Water qs | 100.0 g |

This composition is applied on grey hair containing 90% white hair for 15 minutes. The hair is rinsed and then a pH 3 solution of hydrogen peroxide measuring 12.5 volumes is applied while massaging for 5 minutes.

After rinsing with water and drying, a natural blond coloration of a slightly ashy hue is obtained.

EXAMPLE 4

| | |
| --- | --- |
| 6-Hydroxyindole | 0.8 g |
| 5,6-Dihydroxyindole | 0.3 g |
| Potassium iodide | 1.0 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Hydrochloric acid qs pH = 4.4 | |
| Water qs | 100.0 g |

This composition is applied on grey hair containing 90% white hair for 15 minutes and the hair is then rinsed. A pH 3 solution of hydrogen peroxide measuring 12.5 volumes is then applied for 5 minutes. The hair is again rinsed. The hair is then colored a light chestnut hue.

EXAMPLE 5

| | |
|---|---|
| 4-Hydroxyindole | 1.0 g |
| Potassium iodide | 1.0 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Preservative sold under the name of Germal 115 by the Sutton company | 0.1 g |
| Preservative sold under the name of Nipa Ester 82121 by the Nipa Lab company | 0.3 g |
| Spontaneous pH = 6.5 | |
| Water qs | 100.0 g |

This composition is applied on grey hair containing 90% white hair. After a pause of 15 minutes the hair is rinsed. A pH 3 oxidizing milk measuring 12.5 volumes of hydrogen peroxide is then applied for 5 minutes. The hair is again rinsed and dried. The hair is then colored with a brown hue.

EXAMPLE 6

| | |
|---|---|
| 5,6-Dihydroxyindole | 0.5 g |
| 4-Hydroxyindole | 0.5 g |
| Potassium iodide | 0.8 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Preservative sold under the name of Germal 115 by the Sutton company | 0.1 g |
| Preservative sold under the name of Nipa Ester 82121 by the Nipa Lab company | 0.3 g |
| Spontaneous pH = 6.5 | |
| Water qs | 100.0 g |

This composition is applied on grey hair containing 90% white hair. After a pause of 15 minutes the hair is rinsed. A pH 3 oxidizing milk measuring 12.5 volumes of hydrogen peroxide is then applied for 5 minutes. The hair is again rinsed and dried. The hair is then colored with a chestnut hue.

EXAMPLE 7

| | |
|---|---|
| 4-Hydroxyindole | 0.5 g |
| Potassium iodide | 0.5 g |
| Ethyl alcohol | 10.0 g |
| Hydroxypropylated guar gum sold under the name of Jaguar HP 60 by the Meyhall company | 1.0 g |
| Glycoside alkylether sold at a concentration of 60% AS under the name of Triton CG 110 by the Seppic company | 5.0 g AS |
| Preservative sold under the name of German 115 by the Sutton company | 0.1 g |
| Preservative sold under the name of Nipa Ester 82121 by the Nipa Lab company | 0.3 g |
| pH = 6.5 | |
| Water qs | 100.0 g |

This composition is applied on grey hair containing 90% white hair. After a pause of 15 minutes the hair is rinsed. A pH 3 oxidizing milk measuring 12.5 volumes of hydrogen peroxide is then applied for 5 minutes. The hair is again rinsed and dried. The hair is then colored with a medium ashy hue.

EXAMPLE 8

| | |
|---|---|
| 7-Hydroxyindole | 2.0 g |
| Potassium iodide | 2.0 g |
| Ethyl alcohol | 10.0 g |
| Hydroxypropylated guar gum sold under the name of Jaguar HP 60 by the Celanese company | 1.0 g |
| Glycoside alkylether sold at a concentration of 60% AS under the name of Triton CG 110 by the Seppic company | 5.0 g AS |
| Preservative qs | |
| Spontaneous pH = 6.5 | |
| Water qs | 100.0 g |

This composition is applied for 15 minutes on grey hair containing 90% white hair. The hair is rinsed, then a pH 3 aqueous solution of hydrogen peroxide measuring 12.5 volumes of hydrogen peroxide is applied for 5 minutes. The hair is again rinsed and dried.

Hair dyed a dark mahogany-blond hue is thus obtained.

EXAMPLE 9

The composition of Example 8 is applied for 15 minutes on grey hair containing 90% white hair. After rinsing, a pH 3 aqueous hydrogen peroxide solution measuring 12.5 volumes of hydrogen peroxide is applied for 15 minutes and then the hair is rinsed and dried.

The hair is then dyed with a dark purple-blond hue.

EXAMPLE 10

| | |
|---|---|
| 7-Hydroxyindole | 1.0 g |
| Potassium iodide | 1.0 g |
| Ethyl alcohol | 10.0 g |
| Hydroxypropylated guar gum sold under the name of Jaguar HP 60 by the Celanese company | 1.0 g |
| Glycoside alkylether sold at a concentration of 60% AS under the name of Triton CG 110 by the Seppic company | 5.0 g AS |
| Preservatives qs | |
| Triethanolamine qs pH = 8.5 | |
| Water qs | 100.0 g |

This composition is applied for 15 minutes on grey hair containing 90% white hair. After rinsing, an aqueous solution of hydrogen peroxide, the pH of which is regulated at 8.5 with triethanolamine, and measuring 12.5 volumes of hydrogen peroxide is applied. After 5 minutes exposure, the hair is again rinsed, then light shampooing is performed and the hair is dried.

A pearly blond hue is then obtained on the hair.

EXAMPLE 11

| | |
|---|---|
| 6-Hydroxy-1-methylindole | 2.0 g |
| Ethylene glycol monobutylether | 25.0 g |
| Potassium iodide | 0.8 g |
| Sodium laurylether sulphate containing 2.5 moles of ethylene oxide at 25% AS, sold under the name of Sactipon 8533 by the Lever company | 1.0 g AS |
| Triethanolamine qs pH = 4 | |

-continued

| | |
|---|---|
| Demineralized water qs | 100.0 g |

This composition is applied for 30 minutes on grey hair containing 90% white hair. After rinsing, a pH 3 oxidizing milk measuring 12.5 volumes of hydrogen peroxide is applied to the same hair for 12 minutes. After another rinsing and drying, hair colored a golden blond is obtained.

EXAMPLE 12

| | |
|---|---|
| 6-Hydroxy-1-methylindole | 1.0 g |
| Potassium iodide | 0.8 g |
| Ethyl alcohol | 10.0 g |
| Hydroxypropylated guar gum sold under the name of Jaguar HP60 by the Meyhall company | 1.0 |
| Glycoside alkylether, sold at a concentration of 60% AS under the name of Triton CG 110 by the Seppic company | 5.0 g AS |
| Preservative sold under the name of Germal 115 by the Sutton company | 0.1 g |
| Preservative sold under the name of Nipa Ester 82121 by the Nipa Lab company | 0.3 g |
| Spontaneous pH = 6.5 | |
| Demineralized water qs | 100.0 g |

This composition is applied for 15 minutes on grey hair containing 90% white hair. After rinsing, the hair is treated with a pH 3 oxidizing milk measuring 12.5 volumes of hydrogen peroxide for 5 minutes. After another rinsing and drying, the hair is colored with a dark blond hue with dull highlights.

EXAMPLE 13

| | |
|---|---|
| 3-Methyl-5-hydroxyindole | 1.2 g |
| Ethyl alcohol | 10.0 g |
| Potassium iodide | 0.8 g |
| Guar gum derivative sold under the name of Jaguar HP 60 by the Meyhall company | 1.0 g |
| Glycoside alkylether sold under the name of Triton CG 110 by the Rohm & Haas company | 5.0 g AS |
| Preservatives qs | |
| Triethanolamine qs pH 8 | |
| Demineralized water qs | 100.0 g |

This composition is applied for 15 minutes on grey hair containing 90% white hair. After rinsing, a pH 3 oxidizing milk is applied for 5 minutes. The hair is again rinsed and dried. The hair is then colored with a coppery pearly blond hue.

EXAMPLE 14

| | |
|---|---|
| 5-Hydroxy-2-carboxyindole | 1.0 g |
| Ethyl alcohol | 10.0 g |
| Potassium iodide | 0.5 g |
| Diethylene glycol butylether | 5.0 g |
| Triethanolamine qs pH 7 | |
| Demineralized water qs | 100.0 g |

This composition is applied for 15 minutes on permanent-waved grey hair containing 90% white hair. The hair is rinsed and a pH 3 oxidizing milk measuring 12.5 volumes of hydrogen peroxide is applied for 5 minutes. After rinsing and drying, the hair is colored with a very light beige blond hue.

EXAMPLE 15

| | |
|---|---|
| 6-hydroxy 2,3-dimethyl indole | 1.0 g |
| Ethyl alcohol | 10.0 g |
| Diethyleneglycol butylether | 6.0 g |
| Potassium iodide | 0.8 g |
| Sodium laurylether sulphate containing 2,5 moles of ethylene oxide at 25% AS, sold under the name SACTIPON 8533 by the Lever Company | 1.5 g AS |
| Triethanolamine qs pH 7 | |
| Demineralized water qs | 100.0 g |

This composition is applied for 15 minutes on grey hair containing 90% white hair. After rinsing a pH 3 oxidizing milk measuring 20 volumes of hydrogen peroxide is applied to the same hair for 4 minutes. After another rinsing and drying, the hair is colored with a light beige golden blond shade.

EXAMPLE 16

| | |
|---|---|
| 7-hydroxy 3-methyl indole | 0.8 g |
| Ethyl alcohol | 10.0 g |
| Diethyleneglycol butylether | 7.0 g |
| Potassium iodide | 0.6 g |
| Nonylphenol with 9 moles ethylene oxide sold by Henkel Company under the name SINNOPAL WP9 | 1.5 g |
| Citric acid qs pH 7.5 | |
| Demineralized water qs | 100.0 g |

This composition is applied for 20 minutes on grey hair containing 90% white hair. After rinsing a pH 3 oxidizing milk measuring 12.5 volumes of hydrogen peroxide is applied to the same hair for 5 minutes. After another rinsing and drying, the hair is colored with dark blond mahogany shade.

We claim:

1. A process for dyeing keratin fibers comprising applying to said fibers at least one composition (A) comprising, in a medium suitable for dyeing said fibers, at least one indole colorant having the formula

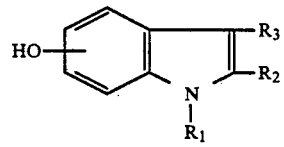

wherein
R$_1$ represents hydrogen or C$_1$-C$_4$ alkyl;
R$_2$ and R$_3$, each independently, represent hydrogen, C$_1$-C$_4$ lower alkyl, carboxyl or C$_1$-C$_4$ alkoxycarbonyl;
the OH radical occupying position 4, 5, 6 or 7, with the proviso that when said OH radical occupies position 5, at least one of R$_1$, R$_2$ or R$_3$ is other than hydrogen,
a salt of said indole or a precursor of said indole,
said indole being present in an amount ranging from 0.01 to 5 percent by weight based on the total weight of said composition, and
(a) a source of iodide ions present in an amount ranging from 0.007 to 4 percent by weight expressed as I$^-$ ions based on the total weight of said composition (A), or (b) a solution of hydrogen peroxide at a concentration of 1–40 volumes having a pH ranging from 2 to 12 when said medium suitable for dyeing said fibers is water or a water-organic solvent mixture, said composition (A) being applied to said keratin fibers either prior to or subsequent to the application to said keratin fibers of a composition (B) comprising, in a medium suitable for dyeing said fibers (i) a solution of hydrogen peroxide at a concentration of 1–40 volumes having a pH ranging from 2–12 when said medium suitable for dyeing said fibers is water or a water-organic solvent mixture, when said composition (A) contains said iodide ions, or (ii) a source of iodide ions present in an amount ranging from 0.007 to 4 percent by weight, expressed as $I^-$ ions, based on the total weight of said composition (B) at a pH ranging from 2 to 11, when said composition (A) contains hydrogen peroxide.

2. The process of claim 1 where in the precursor of said indole the OH group is protected in the OZ form wherein Z is a $C_2$–$C_5$ acyl group.

3. The process of claim 2 wherein Z is an acetyl group.

4. The process of claim 1 wherein said indole colorant is selected from the group consisting of
6-hydroxyindole,
6-hydroxy-1-methylindole,
6-hydroxymethoxy-3-carbonylindole,
6-hydroxy-1-methyl-3-methoxycarbonylindole,
6-acetoxy-1-methyl-3-methoxycarbonylindole,
6-acetoxy-1-methyl-2,3-dimethoxycarbonylindole,
6-acetoxy-1,2-dimethylindole,
6-hydroxy-1,2-dimethylindole,
6-hydroxy-2-methylindole,
6-hydroxy-2-carboxyindole,
6-hydroxy-2,3-dimethylindole,
6-hydroxy-3-carboxyindole,
6-hydroxy-3-ethoxycarbonylindole,
6-hydroxy-2-ethoxycarbonylindole,
6-acetoxyindole,
6-hydroxy-3-methylindole,
7-hydroxyindole,
4-hydroxyindole,
5-hydroxy-3-methylindole,
7-hydroxy-3-methylindole,
5-hydroxy-2-carboxyindole and
5-hydroxy-2-ethoxycarbonylindole.

5. The process of claim 1 wherein said indole colorant is selected from the group consisting of
4-hydroxyindole,
6-hydroxyindole,
7-hydroxyindole,
6-hydroxy-1-methylindole,
5-hydroxy-3-methylindole,
5-hydroxy-2-carboxyindole,
7-hydroxy-3-methylindole and
6-hydroxy-2,3-dimethylindole.

6. The process of claim 1 wherein said composition (A) contains said indole colorant and said source of iodide ions and said composition (B) contains said hydrogen peroxide.

7. The process of claim 1 wherein said composition (B) has a pH ranging from 2 to 9.

8. The process of claim 1 wherein said source of iodide ions is an alkali metal iodide, an alkaline earth metal iodide or ammonium iodide.

9. The process of claim 1 where, in said solution of hydrogen peroxide, said hydrogen peroxide is present in a concentration of 2 to 20 volumes.

10. The process of claim 1 wherein the application of compositions (A) and (B) to said keratin fibers is separated by a rinsing stage.

11. The process of claim 1 wherein each of said composition (A) and (B) is permitted to remain in contact with said fibers for a period of time ranging from 10 seconds to 45 minutes.

12. The process of claim 1 wherein each of said compositions (A) and (B) is permitted to remain in contact with said fibers for a period of time ranging from 2 to 25 minutes.

13. The process of claim 1 wherein said medium suitable for dyeing said fibers in said compositions (A) and (B) is water or a water-solvent mixture.

14. The process of claim 13 wherein said solvent is selected from the group consisting of ethyl alcohol, propyl alcohol, isopropyl alcohol, tert. butyl alcohol, ethylene glycol, ethylene glycol monomethylether, ethylene glycol monoethylether, ethylene glycol monobutylether, diethylene glycol monomethylether, diethylene glycol monoethylether, diethyleneglycol monobutylether, ethylene glycol monomethylether acetate, ethylene glycol monoethylether acetate, propylene glycol, propylene glycol monomethylether, dipropylene glycol monomethylether and methyl lactate.

15. The process of claim 1 wherein said medium suitable for dyeing said fibers is an anhydrous solvent.

16. The process of claim 15 wherein said anhydrous solvent is selected from the group consisting of ethyl alcohol, propyl alcohol, isopropyl alcohol, tert. butyl alcohol, ethylene glycol, ethylene glycol monomethylether, ethylene glycol monoethylether, ethylene glycol monobutylether, diethylene glycol monomethylether, diethylene glycol monoethylether, diethyleneglycol monobutylether, ethylene glycol monomethylether acetate, ethylene glycol monoethylether acetate, propylene glycol, propylene glycol monomethylether, dipropylene glycol monomethylether and methyl lactate.

17. The process of claim 1 wherein said indole colorant is present in said composition (A) in an amount ranging from 0.03 to 3 percent by weight based on the total weight of said composition.

18. The process of claim 1 wherein said source of iodide ions is present in said compositions (A) or (B) in an amount ranging from 0.08 to 1.5 percent by weight, expressed as $I^-$ ions, based on the total weight of said compositions (A) or (B).

19. The process of claim 1 wherein the weight ratio of said indole colorant to said source of iodide ions is between 0.05 and 10.

20. The process of claim 1 wherein the weight ratio of said indole colorant to said source of iodide ions is between 0.5 to 2.

21. The process of claim 1 wherein at least one of said compositions (A) and (B) also contains at least one additive selected from the group consisting of a fatty amide; an anionic, cationic, nonionic or amphoteric surfactant or a mixture thereof; a thickening agent; a fragrance; a sequestering agent; a film-forming agent; a treatment agent; a dispersing agent; a conditioning agent; a preservative; an opacifying agent; and a keratin fiber swelling agent.

22. The process of claim 1 wherein said composition (A) is prepared at the time of use by admixing composition ($A_1$) comprising, in a medium suitable for dyeing said fibers, said indole colorant with composition (A₂) comprising, in a medium suitable for dyeing said fibers, said hydrogen peroxide.

23. The process of claim 1 wherein said composition (A) also contains 5,6-dihydroxyindole or a derivative thereof.

24. The process of claim 1 wherein at least one of said compositions (A) and (B) also contains an oxidation colorant.

25. The process of claim 1 wherein at least one of said compositions (A) and (B) also contains a direct colorant selected from the group consisting of a nitrobenzene dye, an anthraquinone dye, a naphthoquinone dye and a benzoquinone dye.

26. The process of claim 1 wherein said keratin fibers are human hair.

27. A composition for dyeing keratin fibers comprising, in a medium suitable for dyeing said fibers, at least one indole colorant having the formula

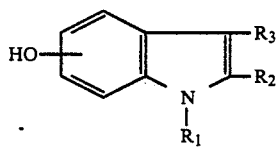

wherein
$R_1$ represents hydrogen or $C_1$-$C_4$ alkyl;
$R_2$ and $R_3$, each independently, represent hydrogen, $C_1$-$C_4$ lower alkyl, carboxyl or $C_1$-$C_4$ alkoxycarbonyl;
the OH radical occupying position 4, 5, 6 or 7, with the proviso that when said OH radical occupies position 5, at least one of $R_1$, $R_2$ or $R_3$ is other than hydrogen,
or a salt of said indole or a precursor of said indole,
said indole being present in an amount ranging from 0.01 to 5 percent by weight based on the total weight of said composition, and
a source of iodide ions present in an amount ranging from 0.007 to 4 percent by weight expressed as I⁻ ions.

28. The composition of claim 27 which also contains 5,6-dihydroxyindole.

29. A multi-compartment kit for dyeing keratin fibers comprising a first compartment containing a composition comprising in a medium suitable for dyeing said keratin fibers at least one indole colorant having the formula

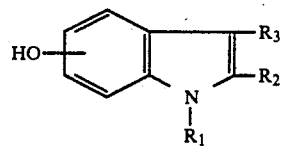

$R_1$ represents hydrogen or $C_1$-$C_4$ alkyl;
$R_2$ and $R_3$, each independently, represent hydrogen, $C_1$-$C_4$ lower alkyl, carboxyl or $C_1$-$C_4$ alkoxycarbonyl;
the OH radical occupying position 4, 5, 6 or 7, with the proviso that when said OH radical occupies position 5, at least one of $R_1$, $R_2$ or $R_3$ is other than hydrogen,
a salt of said indole or a precursor of said indole,
said indole being present in an amount ranging from 0.01 to 5 percent by weight based on the total weight of said composition, and a source of iodide ions present in an amount ranging from 0.007 to 4 percent by weight expressed as I⁻ ions and a second compartment containing an aqueous solution of hydrogen peroxide at a concentration of 1–40 volumes having a pH ranging from 2 to 12.

30. A multi-compartment kit for dyeing keratin fibers comprising
(i) a first compartment containing a composition comprising, in an anhydrous medium suitable for dyeing said fibers, at least one indole coloration having the formula

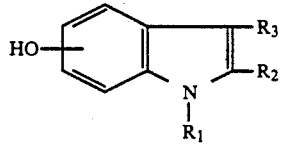

wherein
$R_1$ represents hydrogen or $C_1$-$C_4$ alkyl;
$R_2$ and $R_3$, each independently, represent hydrogen, $C_1$-$C_4$ lower alkyl, carboxyl or $C_1$-$C_4$ alkoxycarbonyl;
the OH radical occupying position 4, 5, 6 or 7, with the proviso that when said OH radical occupies position 5, at least one of $R_1$, $R_2$ or $R_3$ is other than hydrogen,
a salt of said indole or a precursor of said indole,
said indole being present in an amount ranging from 0.01 to 5 percent by weight based on the total weight of said composition, and a source of iodide ions present in an amount ranging from 0.007 to 4 percent by weight expressed as I⁻ ions,
(ii) a second compartment containing an aqueous solution of hydrogen peroxide at a concentration of 1–40 volumes having a pH ranging from 2 to 12, and
(iii) a third compartment containing an aqueous medium to be mixed at the time of use with the contents of said first compartment.

* * * * *